United States Patent
Franzen (10) Patent No.: US 12,402,568 B2
(45) Date of Patent: Sep. 2, 2025

(54) ROUND BALE PRE-COMPLETION YIELD CALCULATION

(71) Applicant: DEERE & COMPANY, Moline, IL (US)

(72) Inventor: Devin M. Franzen, Altoona, IA (US)

(73) Assignee: Deere & Company, Moline, IL (US)

(*) Notice: Subject to any disclaimer, the term of this patent is extended or adjusted under 35 U.S.C. 154(b) by 545 days.

(21) Appl. No.: 18/047,663

(22) Filed: Oct. 19, 2022

(65) Prior Publication Data

US 2024/0130295 A1 Apr. 25, 2024
US 2024/0224878 A9 Jul. 11, 2024

(51) Int. Cl.
| | |
|---|---|
| A01F 15/08 | (2006.01) |
| A01F 15/07 | (2006.01) |
| G01N 9/02 | (2006.01) |
| G01N 33/00 | (2006.01) |

(52) U.S. Cl.
CPC .......... A01F 15/0833 (2013.01); A01F 15/07 (2013.01); G01N 9/02 (2013.01); G01N 33/0098 (2013.01)

(58) Field of Classification Search
CPC ....... A01F 15/0833; A01F 15/07; G01N 9/02; G01N 33/0098
See application file for complete search history.

(56) References Cited

U.S. PATENT DOCUMENTS

| | | | |
|---|---|---|---|
| 10,289,696 B2 | 5/2019 | Derscheid | |
| 2017/0013783 A1* | 1/2017 | Kirk | A01F 15/0883 |
| 2018/0121467 A1* | 5/2018 | Derscheid | G01G 19/414 |
| 2021/0137015 A1* | 5/2021 | Ibuki | A01B 79/005 |

FOREIGN PATENT DOCUMENTS

| | | |
|---|---|---|
| EP | 3315016 A1 | 5/2018 |
| EP | 3679784 A1 | 7/2020 |
| EP | 3818813 A1 | 5/2021 |

OTHER PUBLICATIONS

Extended European Search Report and Written Opinion issued in European Patent Application No. 23199932.7, dated Mar. 15, 2024, in 10 pages.
Wolfgang Buescher et al., Density distribution research of silage round bales with a penetrometer test bench, Land Technik Agricultural Engineering, Jan. 2013, pp. 26-29.

* cited by examiner

*Primary Examiner* — Claude J Brown (57) ABSTRACT

A round baler includes a bale size sensor operable to detect a radial size of a bale during formation thereof, a bale weight sensor operable to detect a weight of a completed bale, and a location sensor operable to determine a respective field origin location of the crop material gathered for each respective one of a plurality of radial layers of the bale. A controller calculates a density of a completed bale with data from the bale weight sensor and the bale size sensor. The controller determines a volume of a respective one of the radial layers during formation of a current bale, subsequent to the completed bale, with data from the bale size sensor. The controller may then estimate a density of the respective one of the radial layers based on the volume of the respective one of the radial layers, and the density of the previously completed bale.

19 Claims, 4 Drawing Sheets

ROUND BALE PRE-COMPLETION YIELD CALCULATION

TECHNICAL FIELD

The disclosure generally relates to a round baler system, and a method of generating a yield map of crop material formed into a round bale with the round baler system.

BACKGROUND

Agricultural balers gather crop material from a field, and compress, the crop material into a bale. A round baler implement shapes the crop material into a cylindrical shape, typically referred to as a round bale. The round baler implement feeds a continuous supply of crop material into a baling chamber to form a round bale. Because of this, the quantity or volume of the crop material required to form a round bale may be gathered from a large area spread throughout the field.

Various crop and harvest management operations may benefit from an accurate yield map showing crop yield across the field. The yield may be considered mass of the crop material per unit area of the field, i.e., a density of the harvested crop material. The density of the crop material may be calculated by multiplying a known or determined volume by a known or determined weight. For a round bale, the density of the crop material is generally determined by sensing a size and weight of a completed round bale. These values may then be multiplied to calculate the density of the completed round bale. As such, the yield map is limited to the density of the completed round bale as a whole spread across the entire region of the field from which the crop material was gathered for that specific round bale.

Yield maps based on this average bale density described above are therefore generalized and lack the desired level of detail or specificity. Additionally, the yield maps described above are latent because they require completion of a specific bale to calculate the yield from that specific bale. As such, the generation of the yield map is post processing of the completed round bale, which may reduce the value of the yield map for certain harvest operations.

SUMMARY

A round baler system is provided. The round baler system includes a pick-up operable to gather and move crop material while traversing a field. A baler system having a baling chamber configured to receive a flow of crop material from the pick-up and roll the incoming flow of crop material in a spiral fashion into a bale having a cylindrical shape. The bale includes a plurality of radial layers. A bale size sensor is operable to detect data related to a radial size of the bale during formation thereof. A bale weight sensor is operable to detect data related to a weight of a completed bale. A location sensor is operable to determine a respective field origin location of the crop material gathered by the pick-up for each respective one of the plurality of radial layers of the bale. A controller is disposed in communication with the bale size sensor, the bale weight sensor, and the location sensor. The controller includes a processor and a memory having a yield mapping algorithm stored thereon. The processor is operable to execute the yield mapping algorithm to calculate a density of a completed bale with data received from the bale weight sensor and the bale size sensor. The controller is operable to determine a volume of a respective one of the plurality of radial layers during formation of a current bale subsequent to the completed bale with data received from the bale size sensor. The controller may then estimate a density of the respective one of the plurality of radial layers during formation of the current bale based on the volume of the respective one of the plurality of radial layers, and the density of the completed bale.

In one aspect of the disclosure, the baler system may further include a moisture sensor that is operable to detect data related to a moisture content of the crop material for each respective one of the plurality of radial layers. The processor may be operable to execute the yield mapping algorithm to determine a moisture content of the crop material of the respective one of the plurality of radial layers during formation of the current bale with data received from the moisture sensor, and estimate the density of the respective one of the plurality of radial layers during formation of the current bale based on the volume of the respective one of the plurality of radial layers, the moisture content of the respective one of the plurality of radial layers, and the density of the completed bale.

In one aspect of the disclosure, the processor is operable to execute the yield mapping algorithm to estimate the density of the respective one of the plurality of radial layers during formation of the current bale based on the density of at least two previously completed bales. For example, the processor may use a running average or a weighted average of the prior 2, 3, . . . , n, fully completed bales to estimate the density of the radial layer of the current bale during formation thereof.

In one aspect of the disclosure, the processor is operable to execute the yield mapping algorithm to estimate a density of each of the plurality of radial layers of the current bale during formation of the current bale. Accordingly, the controller may estimate the yield of each respective radial layer based on the moisture content of that respective layer, the volume of that respective layer, and the density of one or more previously completed bales. By doing so, the detail and granularity of the yield data is greatly increased.

In one aspect of the disclosure, the processor is operable to execute the yield mapping algorithm to determine a field origin location of the respective one of the plurality of radial layers during formation of the current bale. The processor may be operable to execute the yield mapping algorithm to generate a yield map of the field based on the estimated density and the field origin location of the respective one of the plurality of radial layers during formation of the current bale. As such, the yield map is generated based on the yield of each individual radial layer of the bale and the associated portion of the field from which crop material was gathered for that specific radial layer. By so doing, the detail of the yield map is greatly increased from previous yield map data based on the average yield of the entire completed bale.

In one aspect of the disclosure, the processor may be operable to execute the yield mapping algorithm to control a function of the baler system based on the yield map of the field. Because the yield map provides highly detailed data during formation of the bale, instead of post bale processing, the yield map may be used to predict harvest ahead of the baler system, and thereby control the operation of the baler system in real time. For example, the function of the baler system may include path planning for the baling operation, weaving control of the baler system to evenly distribute crop material across a width of the baling chamber, a speed of movement across the field, a secondary crop processing function, a forming belt tension, a bale drop location, etc.

In one aspect of the disclosure, a method of generating a yield map of crop material formed into a round bale is provided. The method includes completely forming a first bale in a baling chamber of a baler system. A density of the first bale may then be calculated after the first bale is completely formed. A second bale may then be formed in the baling chamber of the baler system. The second bale is formed via a plurality of radial layers radially stacked one on top of another. A volume of a respective one of the plurality of radial layers of the second bale may then be determined during formation of the second bale, and subsequent to the completed first bale, with data received from a bale size sensor. A moisture content of the crop material of the respective one of the plurality of radial layers of the second bale may be determined during formation of the second bale with data received from a moisture sensor. A density of the respective one of the plurality of radial layers of the second bale may then be estimated during formation of the second bale based on the volume and the moisture content of the respective one of the plurality of radial layers of the second bale, and the density of the completed first bale. A field origin location of the respective one of the plurality of radial layers of the second bale is determined during formation of the second bale. The yield map of the field may then be generated by a controller based on the estimated density and the field origin location of the respective one of the plurality of radial layers of the second bale during formation of the second bale.

In one aspect of the controller the method described herein may further include controlling a function of the baler system based on the yield map of the field. Because the yield map provides highly detailed data during formation of the bale, instead of post bale processing, the yield map may be used to predict harvest ahead of the baler system, and thereby control the operation of the baler system in real time. For example, the function of the baler system may include path planning for the baling operation, weaving control of the baler system to evenly distribute crop material across a width of the baling chamber, a speed of movement across the field, a secondary crop processing function, a forming belt tension, a bale drop location, etc.

The above features and advantages and other features and advantages of the present teachings are readily apparent from the following detailed description of the best modes for carrying out the teachings when taken in connection with the accompanying drawings.

DETAILED DESCRIPTION

Those having ordinary skill in the art will recognize that terms such as "above," "below," "upward," "downward," "top," "bottom," etc., are used descriptively for the figures, and do not represent limitations on the scope of the disclosure, as defined by the appended claims. Furthermore, the teachings may be described herein in terms of functional and/or logical block components and/or various processing steps. It should be realized that such block components may be comprised of any number of hardware, software, and/or firmware components configured to perform the specified functions.

Terms of degree, such as "generally", "substantially" or "approximately" are understood by those of ordinary skill to refer to reasonable ranges outside of a given value or orientation, for example, general tolerances or positional relationships associated with manufacturing, assembly, and use of the described embodiments.

As used herein, "e.g." is utilized to non-exhaustively list examples, and carries the same meaning as alternative illustrative phrases such as "including," "including, but not limited to," and "including without limitation." As used herein, unless otherwise limited or modified, lists with elements that are separated by conjunctive terms (e.g., "and") and that are also preceded by the phrase "one or more of," "at least one of," "at least," or a like phrase, indicate configurations or arrangements that potentially include individual elements of the list, or any combination thereof. For example, "at least one of A, B, and C" and "one or more of A, B, and C" each indicate the possibility of only A, only B, only C, or any combination of two or more of A, B, and C (A and B; A and C; B and C; or A, B, and C). As used herein, the singular forms "a", "an" and "the" are intended to include the plural forms as well, unless the context clearly indicates otherwise. Further, "comprises," "includes," and like phrases are intended to specify the presence of stated features, steps, operations, elements, and/or components, but do not preclude the presence or addition of one or more other features, steps, operations, elements, components, and/or groups thereof.

Figure 1:
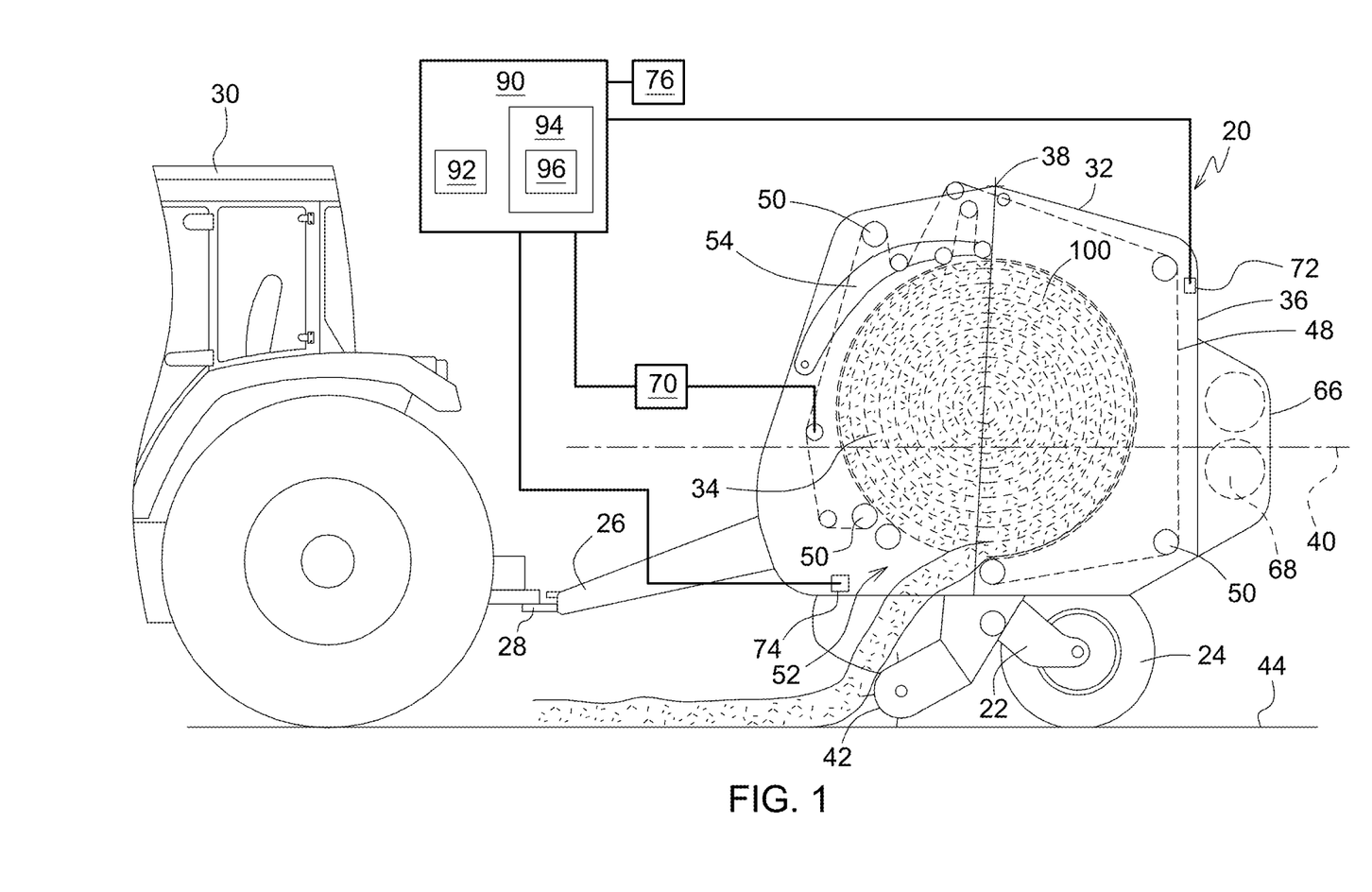
FIG. 1 is a schematic side view of a round baler system.

Referring to FIG. 1, a baler system is generally shown at 20. The baler system 20 may alternatively be referred to herein as a round baler 20. The round baler 20 includes a frame 22. One or more ground engaging elements 24, such as but not limited to one or more wheels and/or tracks, are attached to and rotatably supported by the frame 22. A tongue 26 may be coupled to the frame 22 at a forward end of the frame 22. A hitch arrangement 28 may be included with the tongue 26. The hitch arrangement 28 may be used to attach the round baler 20 to a traction unit 30, such as but not limited to an agricultural tractor. In other embodiments, the round baler 20 may be self-propelled, in which case the traction unit 30 and the round baler 20 are configured as a single, self-propelled vehicle.

The round baler 20 includes a housing 32 forming a baling chamber 34. The housing 32 is attached to and supported by the frame 22. The housing 32 may include one or more walls or panels that at least partially enclose and/or define the baling chamber 34. The round baler 20 further includes a gate 36. The gate 36 is attached to and rotatably supported by the housing 32. The gate 36 is positioned adjacent a rearward end of the frame 22 and is pivotably moveable about a gate axis 38. The gate axis 38 is generally horizontal and perpendicular to a central longitudinal axis 40 of the frame 22. The gate 36 is moveable between a closed position for forming a bale 100 within the baling chamber 34, and an open position for discharging the bale 100 from the baling chamber 34.

The round baler 20 includes a pick-up 42 positioned proximate the forward end of the frame 22. The pickup gathers crop material from a ground surface 44 of a field 46 as the round baler 20 traverses the field 46. The pickup directs the gathered crop material toward and into an inlet 52 of the baling chamber 34. The pickup may include, but is not limited to tines, forks, augers, conveyors, baffles, etc., for gathering and moving the crop material. The round baler 20 may be equipped with a pre-cutter, disposed between the pickup and the inlet 52 of the baling chamber 34. As such, the pre-cutter is disposed downstream of the pickup and upstream of the inlet 52 relative to a direction of travel of the crop material. The pre-cutter cuts or chops the crop material into smaller pieces.

The round baler 20 may be configured as a variable chamber baler, or as a fixed chamber baler. The round baler 20 shown in FIG. 1 and described herein is depicted and described as a variable chamber baler. As is understood by those skilled in the art, the variable chamber baler includes a plurality of longitudinally extending side-by-side forming belts 48 that are supported by a plurality of rollers 50. The bale 100 is formed by the forming belts 48 and one or more side walls of the housing 32.

The crop material is directed through the inlet 52 and into the baling chamber 34, whereby the forming belts 48 roll the crop material in a spiral fashion into the bale 100 having a cylindrical shape. The belts apply a constant pressure to the crop material as the crop material is formed into the bale 100. A belt tensioner 54 continuously moves the forming belts 48 radially outward relative to a center of the cylindrical bale 100 as the diameter 58 of the bale 100 increases. The belt tensioner 54 maintains the appropriate tension in the belts to obtain the desired density of the crop material.

Figure 2:
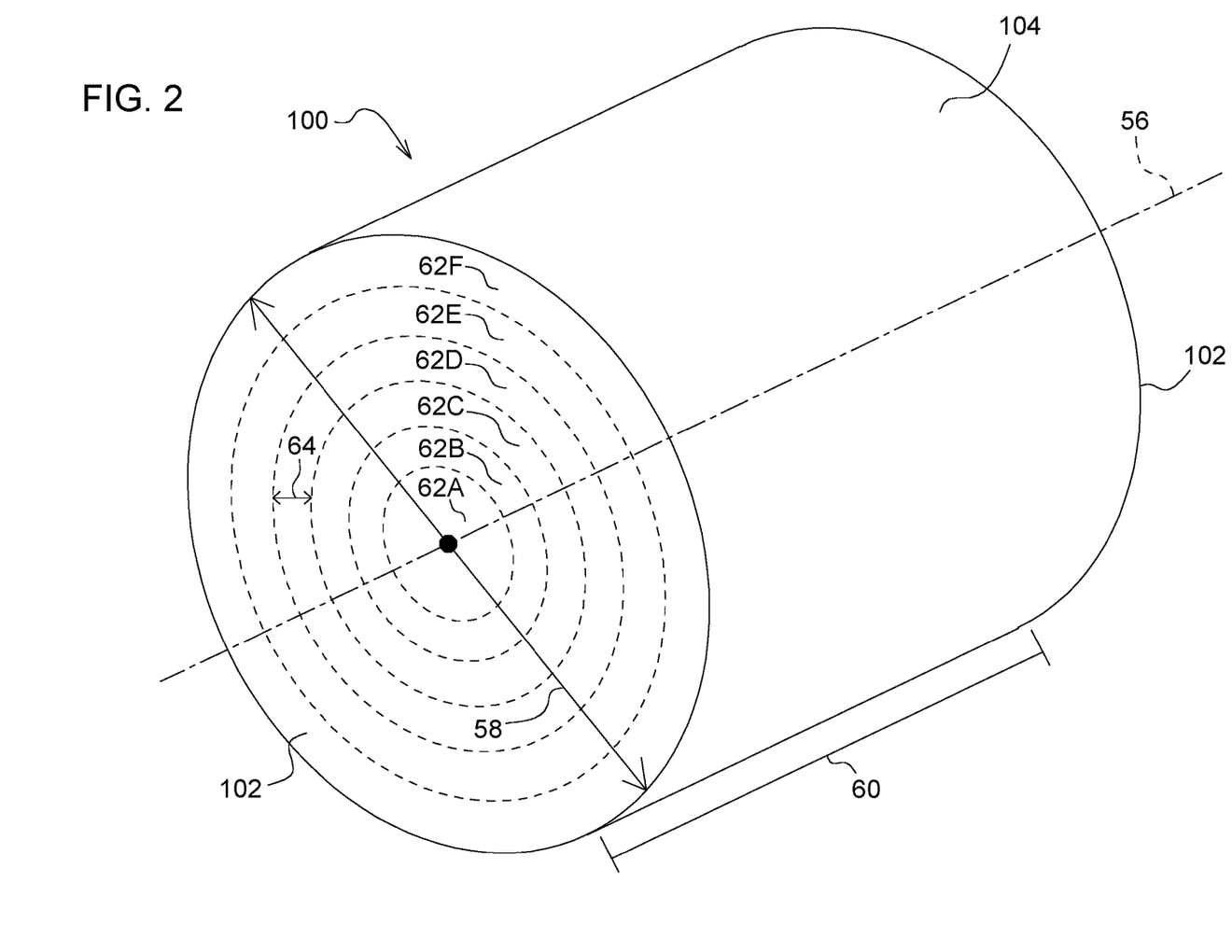
FIG. 2 is a schematic perspective view of a round bale
Figure 3:
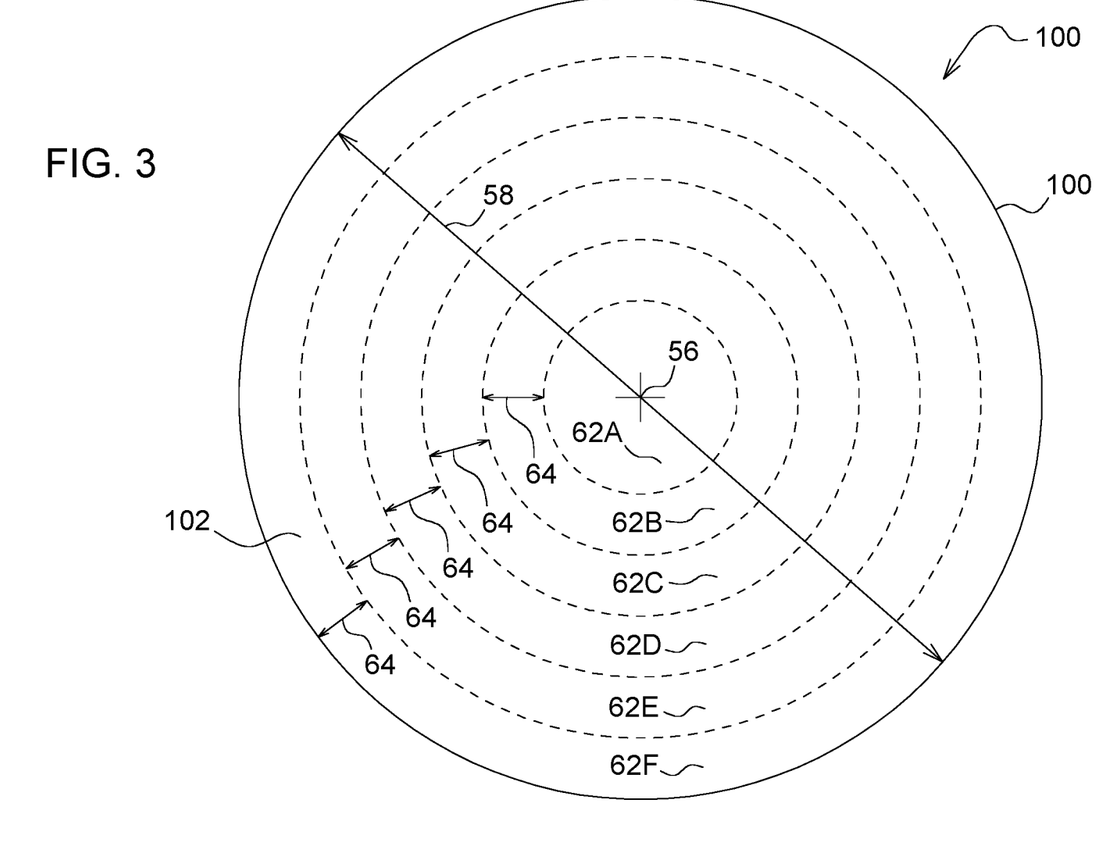
FIG. 3 is a schematic end view of the round bale.

Referring to FIGS. 2 and 3, the cylindrical shape of the formed bale 100 includes a center axis 56 of the bale 100. Circular end faces 102 of the bale 100 are positioned at axial ends of the bale 100 along the center axis 56. The circular end faces 102 of the bale 100 include and/or define a diameter 58 of the bale 100. The bale 100 includes an exterior circumferential surface 104 extending between the circular end faces of the bale 100 a length 60. The length 60 of the bale 100 is generally fixed and/or defined by a width of the baling chamber 34. However, the diameter 58 of the bale 100 may be controlled by the baler system 20.

The bale 100 may be sectioned and/or partitioned into a plurality of radial layers 62. Each radial layer 62 includes a radial thickness 64 extending transverse to the center axis 56 of the bale 100, and extends the length 60 of the bale 100 between the circular end faces 102 of the bale 100. As such, a first radial layer 62 may be defined at the center of the bale 100 by a solid cylindrical shape, whereas each progressive outer radial layer is positioned radially outward from the first radial layer 62, and is defined by a hollow cylindrical shape. For example, a second radial layer 62 is shown at 62B, a third radial layer 62 is shown at 62C, a fourth radial layer 62 is shown at 62D, etc. The bale 100 may be partitioned into any number of radial layers 62. A greater number of the radial layers 62 generally corresponds to a higher level of resolution and increased accuracy of a yield map 98, described in greater detail below. The radial thickness 64 of each respective radial layer 62 may be defined as a constant, or may be varied, such that each of the respective radial layers 62 has a different radial thickness 64. In other implementations, the radial layers 62 may be grouped into sets, with each respective radial layer 62 within a given set of layers having a similar radial thickness 64, and different sets of radial layers 62 having a substantially different radial thickness 64. In one example implementation, the bale 100 may be partitioned into between ten and twenty radial layers 62.

In another implementation the bale 100 may be portioned into the plurality of radial layers 62 based on the formation of the bale 100. As described above, the bale 100 is formed in a spiral fashion by rotating the bale 100 within the baling chamber 34. As such, each respective radial layer 62 may be defined based on a single rotation of the bale 100 within the baling chamber 34. In other words, each rotation of the bale 100 in the baling chamber 34 forms a successive radial layer 62 of the bale 100. The radial thickness 64 of the radial layers 62 defined in such a manner may be variable, based on the amount of crop material used in the formation of that respective radial layer 62 and the density of the crop material in that respective radial layer 62.

Referring to FIG. 1, the round baler 20 includes a wrap system 66. The wrap system 66 is operable to wrap the bale 100 with a wrap material 68 inside the baling chamber 34. Once the bale 100 is formed to a desired size, the wrap system 66 feeds the wrap material 68 into the baling chamber 34 to wrap the bale 100 and thereby secure the crop material in a tight package and maintain the desired shape of the bale 100. The wrap material 68 may include, but is not limited to, a twine, a net mesh, or a solid plastic wrap. Movement of the gate 36 into the open position simultaneously moves the belts clear of the formed bale 100, and allows the formed and wrapped bale 100 to be discharged through the rear of the baling chamber 34.

The baler system 20 includes a bale size sensor 70 that is operable to detect data related to a radial size of the bale 100 during formation thereof. In one implementation, the bale size sensor 70 is operable to detect the radial size of each radial layer 62 of the bale 100 during formation of the bale 100. For example, if the radial layers 62 are defined to include the thickness of the layer formed during a single rotation of the bale 100 in the baling chamber 34, then the bale size sensor 70 may detect data related to the radial size of the bale 100 at the beginning and end of each rotation of the bale 100 in the baling chamber 34. In another implementation, the bale size sensor 70 may include location and time data related to the radial size of the bale 100 during formation, such that the location and time of each respective radial layer 62 of the bale 100 may be determined by a controller 90, described in greater detail below. The baler size sensor may include a device that is capable of detecting or sensing data related to the radial size of the bale 100. For example, the bale size sensor 70 may include, but is not limited to, and optical sensor positioned to capture an image of the bale 100 from which the radial size of the bale 100 may be determined, or position sensor, e.g., a potentiometer, that is positioned and arranged to detect a position of a component of the baler system 20 related to the radial size of the bale 100, such as but not limited to an belt tensioning arm of the baler system 20. It should be appreciated that the bale size sensor 70 may include some other device that senses some other type of data not described herein that may be used to determine the radial size of the bale 100.

The baler system 20 further includes a bale weight sensor 72. The bale weight sensor 72 is operable to detect data related to a weight of the bale 100. In one implementation, the bale weight sensor 72 may detect the weight of at least the completed bale 100. However, in other implementations, the baler weight sensor may detect the weight of the bale 100 from beginning through completion, i.e., detect the changing weight of the bale 100 during formation and at completion. The bale weight sensor 72 may include a device that is capable of detecting data related to the weight of the bale 100. For example, the bale weight sensor 72 may include a force sensor positioned and arranged to detect a weight of the while in the baling chamber 34, such as detecting a force and/or strain on an axle or component thereof. In other implementations, the bale weight sensor 72 may include a force sensor operable to detect the force and/or strain of a component used to hold or lift the bale 100. For example, the bale weight sensor 72 may include a force sensor positioned and operable to detect a force exerted by a hydraulic cylinder associated with the lift gate 36 used to lift the completed bale 100 out of the baling chamber 34 post completion. It should be appreciated that the bale weight sensor 72 may include some other device that senses some other type of data not described herein that may be used to determine the weight of the bale 100.

The baler system 20 may further include a moisture sensor 74 that is operable to detect data related to a moisture content of the crop material for each respective one of the plurality of radial layers 62. The moisture sensor 74 may include for example, but is not limited to, a Near Infra-Red light spectrum optical sensor capable of detecting images in the NIR light spectrum, which may be used to determine the moisture content of the crop material. The moisture sensor 74 may be positioned to detect the moisture level of the crop material either in the baling chamber 34, or outside the baling chamber 34 in the flow of crop material entering the baling chamber 34, such as proximate the inlet 52 of the baling chamber 34. The data from the moisture sensor 74 may associated with the specific crop material used to form a respective radial layer 62 of the bale 100. For example, with the beginning of each rotation of the bale 100 within the baling chamber 34, the moisture sensor 74 data may be associated with the respective radial layer 62 of the bale 100 being formed. Upon the completion of a respective radial layer 62 of the bale 100, the data from the moisture sensor 74 may be associated the next radial layer 62 of the bale 100.

Figure 4:
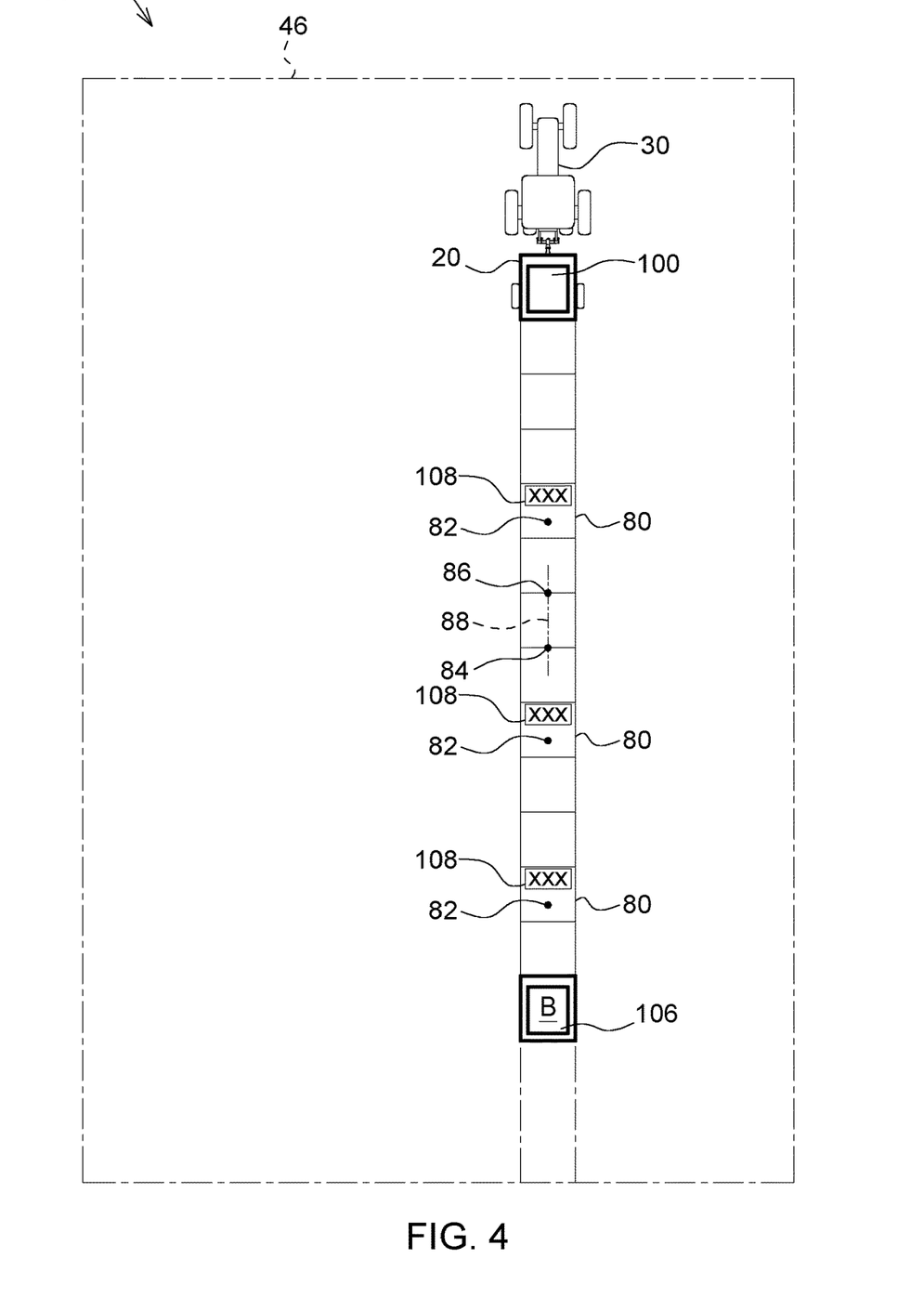
FIG. 4 is a schematic plan view of a yield map representing a field.

As shown in FIG. 1, the baler system 20 further includes a location sensor 76. Referring to FIG. 4, the location sensor 76 is operable to determine a respective field origin location 78 of the crop material gathered by the pick-up 42 for each respective one of the plurality of radial layers 62. The field origin location 78 of the crop material for each radial layer 62 may include a coordinate or other positional identification of the region of the field 46 from which the crop material used to form that respective radial layer 62 of the bale 100 was gathered. The field origin location 78 may include, but is not limited to, an boundary 80 of a region outlining the area of the field 46 from which the crop material of that respective radial layer 62 of the bale 100 was gathered, a centroid location 82 of a region of standardized size representing the region outlining the area of the field 46 from which the crop material of that respective radial layer 62 of the bale 100 was gathered, or a beginning location 84 and an ending location 86 of a track 88 having a defined width outlining or representing the area of the field 46 from which the crop material of that respective radial layer 62 of the bale 100 was gathered. The location sensor 76 may include, but is not limited to, a device capable of sensing data that may be used to determine a geographic location within the field 46. For example, the location sensor 76 may include, but is not limited to, a Global Positioning System sensor that is operable to receive satellite signals and triangulate a position location therefrom as is understood in the art.

As noted above, the baler system 20 includes a controller 90. The controller 90 is disposed in communication with the bale size sensor 70, the bale weight sensor 72, the moisture sensor 74, and the location sensor 76. While the controller 90 is generally described herein as a singular device, it should be appreciated that the controller 90 may include multiple devices linked together to share and/or communicate information therebetween. Furthermore, it should be appreciated that the controller 90 may be located on the round baler 20 implement or located remotely from the round baler 20 implement, such as on an associated traction unit 30, e.g., tractor.

The controller 90 may alternatively be referred to as a computing device, a computer, a control unit, a control module, a module, etc. The controller 90 includes a processor 92, a memory 94, and all software, hardware, algorithms, connections, sensors, etc., necessary to manage and control the operation of the baler system 20. As such, a method may be embodied as a program or algorithm operable on the controller 90. It should be appreciated that the controller 90 may include any device capable of analyzing data from various sensors, comparing data, making decisions, and executing the required tasks.

As used herein, "controller 90" is intended to be used consistent with how the term is used by a person of skill in the art, and refers to a computing component with processing, memory, and communication capabilities, which is utilized to execute instructions (i.e., stored on the memory or received via the communication capabilities) to control or communicate with one or more other components. In certain embodiments, the controller 90 may be configured to receive input signals in various formats (e.g., hydraulic signals, voltage signals, current signals, CAN messages, optical signals, radio signals), and to output command or communication signals in various formats (e.g., hydraulic signals, voltage signals, current signals, CAN messages, optical signals, radio signals).

The controller 90 may be in communication with other components on the baler system 20, such as hydraulic components, electrical components, and operator inputs within an operator station of an associated work vehicle. The controller 90 may be electrically connected to these other components by a wiring harness such that messages, commands, and electrical power may be transmitted between the controller 90 and the other components. Although the controller 90 is referenced in the singular, in alternative implementations the configuration and functionality described herein can be split across multiple devices using techniques known to a person of ordinary skill in the art.

The controller 90 may be embodied as one or multiple digital computers or host machines each having one or more processors 92, read only memory (ROM), random access memory (RAM), electrically-programmable read only memory (EPROM), optical drives, magnetic drives, etc., a high-speed clock, analog-to-digital (A/D) circuitry, digital-to-analog (D/A) circuitry, and any required input/output (I/O) circuitry, I/O devices, and communication interfaces, as well as signal conditioning and buffer electronics.

The computer-readable memory 94 may include any non-transitory/tangible medium which participates in providing data or computer-readable instructions. The memory 94 may be non-volatile or volatile. Non-volatile media may include, for example, optical or magnetic disks and other persistent memory. Example volatile media may include dynamic random access memory (DRAM), which may constitute a main memory. Other examples of embodiments for memory 94 include a floppy, flexible disk, or hard disk, magnetic tape or other magnetic medium, a CD-ROM, DVD, and/or any other optical medium, as well as other possible memory devices such as flash memory.

The controller 90 includes the tangible, non-transitory memory 94 on which are recorded computer-executable instructions, including a yield mapping algorithm 96. The processor 92 of the controller 90 is configured for executing the yield mapping algorithm 96. The yield mapping algorithm 96 implements a method of generating a yield map 98 and controlling the baler system 20, described in detail below.

Referring to FIG. 4, the process begins by completely forming a first bale 106 in the baling chamber 34 of the baler system 20. The controller 90 may then calculate a density of the completed first bale 106 with data received from the bale weight sensor 72 and the bale size sensor 70. The bale size sensor 70 may communicate a data signal to the controller 90 including information related to the size of the first bale 106. In one implementation, the length 60 of the first bale 106 may be presumed based on the width of the baling chamber 34. The data from the bale size sensor 70 may relate, for example, to the diameter 58 of the first bale 106. The controller 90 may then calculate a total volume of the first bale 106 from the data related to the diameter 58 of the first bale 106 and the known length 60 of the first bale 106. The bale weight sensor 72 may communicate a data signal to the controller 90 including information related to the weight of the first bale 106. The controller 90 may then calculate the weight of the completed first bale 106. Having determined the volume and weight of the first bale 106, the controller 90 may then calculate the density of the completed first bale 106 by, for example, dividing the weight by the volume.

Once the first bale 106 has been completely formed, the first bale 106 may be ejected from the baling chamber 34, after which a second bale 100 may be formed in the baling chamber 34 of the baler system 20. As described above, the second bale 100 may be segmented into the plurality of radial layers 62. In one implementation, each of the radial layers 62 may be defined based on a pre-set radial thickness 64. In another implementation, each of the radial layers 62 may be defined based on a set number of rotations of the bale 100 in the baling chamber 34, e.g., a single rotation, two rotations, etc., in which case the radial thickness 64 of each layer will vary and is dependent upon the amount or volume of crop material supplied to the baling chamber 34 while forming a particular radial layer 62.

The process described below may be used for each of the plurality of radial layers 62 in succession during formation of the second bale 100 in the forming chamber. The description below describes the process for a single one of the plurality of radial layers 62. However, it should be appreciated that the process is repeated for each of the plurality of radial layers 62 of the second bale 100.

During formation of a current bale 100, e.g., the second bale 100 which is formed subsequent to the completed first bale 106, each of the plurality of radial layers 62 is formed in succession. Upon the completion of a respective one of the radial layers 62 of the second bale 100, the controller 90 determines a volume of that respective one of the radial layers 62 with data received from the bale size sensor 70. The data received from the bale size sensor 70 may include, but is not limited to, data related to a radial or diametric size of the second bale 100 at the beginning of the respective radial layer 62 and a radial or diametric size of the second bale 100 at the end or completion of the respective radial layer 62. Knowing the diameter 58 of the second bale 100 at the beginning and end of the respective radial layer 62, and knowing the length 60 of the bale 100 (which is generally a standard dimension based on the width of the baling chamber 34), the controller 90 may calculate the volume of the respective radial layer 62. It should be appreciated that the data from the bale size sensor 70 may differ from the example implementation described herein, and the process in which the controller 90 calculates or determines the volume of the respective radial layer 62 may differ from the example implementation described herein based on the type of data form the bale size sensor 70.

The controller 90 may further determine a moisture content of the crop material of the respective one of the radial layers 62 during formation of the current, e.g., the second bale 100. The controller 90 may determine the moisture content from data received from the moisture sensor 74. For example, the controller 90 may continuously sense the moisture content of the crop material entering the baling chamber 34. Based on a defined start time and end time of the formation of the respective radial layer 62, the controller 90 may associate the moisture content of the crop material measured during these time periods with the respective radial layer 62, and calculate an average moisture content from the measured values associated with the respective layers. It should be appreciated that the data from the moisture sensor 74 may differ from the example implementation described herein, and the process in which the controller 90 calculates or determines the moisture content of the respective radial layer 62 may differ from the example implementation described herein based on the type of data form the moisture sensor 74.

Using the determined volume of respective radial layer 62 and the moisture content of the crop material forming the respective radial layer 62, in combination with the density of the completed first bale 106, the controller 90 may then estimate a density of the respective radial layer 62 during formation of the second bale 100. The controller 90 may use machine learning techniques known to those skilled in the art to estimate the density of the respective radial layer 62. The density of the first bale 106, in combination with and/or modified by the moisture content of the respective radial layer 62, may be used to provide an accurate estimate of the density of the respective radial layer 62 during formation of the second bale 100. As such, the estimate of the density of the respective radial layer 62 of the second bale 100 may be calculated during formation of the second bale 100, without having to wait until the second bale 100 is completed.

In one implementation of the disclosure, the controller 90 may use the density of more than one previously completed bale, e.g., the first bale 106 to estimate the density of the respective radial layer 62 of the second bale 100. For example, the controller 90 may use the density of two or more previously completed bales to estimate the density of the respective radial layer 62 of the second bale 100. In one example, the controller 90 may use a running average of previously completed bales to estimate the density of the respective radial layer 62 of the second bale 100. In another example, the controller 90 may use a weighted average of previously completed bales, in which more recently completed bales are weighted higher than less recent completed bales.

It is contemplated that the density of the current bale 100 may change as the radial and/or diametric size 58 of the bale 100 increases during formation. For example, the density of the bale 100 may increase as the radial and/or diametric size 58 of the bale 100 increases. As such, the density of each respective one of the plurality of radial layers 62A, 62B, 62C, 62D, 62E, 62F, may change as the radial and/or diametric size 58 of the bale 100 increases during formation. To account for this, the controller 90 may estimate the density of each of the radial layers 62A, 62B, 62C, 62D, 62E, 62F of the current bale 100 during formation of the current bale 100 based on a respective diametric size 58 of each of the radial layers 62A, 62B, 62C, 62D, 62E, 62F of the current bale 100. For example, the controller may estimate the density of each of the plurality of radial layers 62A, 62B, 62C, 62D, 62E, 62F of the current bale 100 during formation of the current bale 100 by multiplying the estimated density of each respective one of the plurality of radial layers 62A, 62B, 62C, 62D, 62E, 62F by a density factor. The density factor may be based on the radial and/or diametric size 58 of that respective radial layer 62A, 62B, 62C, 62D, 62E, 62F. The density factor may include a number equal to or less than one. For example, a respective radial layer 62B located near the first or center radial layer 62A may have a lesser density than a respective radial layer 62F located near the exterior circumferential surface 104 of the current bale 100. As such, the respective radial layer 62B located near the center radial layer 62A may be associated with and the estimated density thereof multiplied by a density factor of, for example, 0.75 to decrease the estimated density of that respective radial layer 62B, whereas the respective radial layer 62F located near the exterior circumferential surface 104 of the current bale 100 may be associated with and the estimated density thereof multiplied by a density factor of, for example, 1.00 to not decrease the estimated density of that respective radial layer 62F. The adjusted values of the estimated densities of each respective radial layer 62A, 62B, 62C, 62D, 62E, 62F of the current bale 100, i.e., the estimated density multiplied by the respective density factor, may then be used to define the yield map 98.

The controller 90 further determines the field origin location 78 of the respective radial layer 62 during formation of the second bale 100, with data from the location sensor 76. As described above, the field origin location 78 of the crop material for each radial layer 62 may include a coordinate or other positional identification of the region of the field 46 from which the crop material used to form that respective radial layer 62 of the bale 100 was gathered. The field origin location 78 may include, but is not limited to, an boundary of a region outlining the area of the field 46 from which the crop material of that respective radial layer 62 of the bale 100 was gathered, a centroid location 82 of a region of standardized size representing the region outlining the area of the field 46 from which the crop material of that respective radial layer 62 of the second bale 100 was gathered, or a beginning location 84 and an ending location 86 of a track 88 having a defined width outlining or representing the area of the field 46 from which the crop material of that respective radial layer 62 of the second bale 100 was gathered. The controller 90 may use data from the location sensor 76 to determine the field origin location 78 of the crop material gathered by the pick-up 42 for the respective radial layer 62 of the second bale 100.

Referring to FIG. 4, the controller 90 may then generate a yield map 98 of the field 46 based on the estimated density and the field origin location 78 of the respective radial layer 62 during formation of the second bale 100. Accordingly, the yield map 98 may be updated on real time during formation of the second bale 100, reflecting the yield data from the second bale 100, before the second bale 100 is fully completed. The yield map 98 may identify the quantity of crop harvested from various regions of the field 46 by calculating the quantity of the crop in each respective radial layer 62 from the density thereof, and associating that quantity of crop to the region of the field 46 from which it was gathered to form that respective radial layer 62. As shown in FIG. 4, the respective boundaries 80 for each of the plurality of radial layers 62 are generally shown. The yield map 98 may include indicia 108 for each respective boundary 80 indicating the weight of the crop material gathered from that section of the field 46 for that respective radial layer 62. As noted above, the process described herein may be performed for each of the plurality of radial layers 62 of the second bale 100. Because the yield data is based on the density of each individual radial layer 62 of the second bale 100, the granularity and detail of the yield map 98 is increased when compared to a yield map 98 generated only from a fully completed bale 100.

Additionally, because the yield map 98 may be updated in real time, the controller 90 may be configured to control a function of the baler system 20 based on the yield map 98 of the field 46. Because the yield map 98 provides highly detailed data during formation of the bale 100, instead of post bale 100 processing, the yield map 98 may be used to predict harvest ahead of the baler system 20, and thereby control the operation of the baler system 20 in real time. For example, the function of the baler system 20 may include, but is not limited to, path planning for the baling operation, weaving control of the baler system 20 to evenly distribute crop material across a width of the baling chamber 34, a speed of movement across the field 46, a secondary crop processing function, a forming belt tension, a bale drop location, etc. In order to control one of the functions described above, the controller 90 may be coupled to and configured to control a steering system of the associated work vehicle, a trailing position of the baler system 20, a pre-cutter setting, a speed of the associated work vehicle, a desired bale density, an bale accumulator associated with the baler system 20, etc.

The detailed description and the drawings or figures are supportive and descriptive of the disclosure, but the scope of the disclosure is defined solely by the claims. While some of the best modes and other embodiments for carrying out the claimed teachings have been described in detail, various alternative designs and embodiments exist for practicing the disclosure defined in the appended claims.

What is claimed is:

1. A round baler system comprising:
a pick-up operable to gather and move crop material while traversing a field;
a baler system having a baling chamber configured to receive a flow of material from the pick-up and roll the incoming flow of crop material in a spiral fashion into a bale having a cylindrical shape, wherein the bale includes a plurality of radial layers;
a bale size sensor operable to detect data related to a radial size of the bale during formation thereof;
a bale weight sensor operable to detect data related to a weight of a completed bale;
a location sensor operable to determine a respective field origin location of the crop material gathered by the pick-up for each respective one of the plurality of radial layers;
a controller including a processor and a memory having a yield mapping algorithm stored thereon, wherein the processor is operable to execute the yield mapping algorithm to:
calculate a density of a completed bale with data received from the bale weight sensor and the bale size sensor;
determine a volume of a respective one of the plurality of radial layers during formation of a current bale subsequent to the completed bale with data received from the bale size sensor; and
estimate a density of the respective one of the plurality of radial layers during formation of the current bale based on the volume of the respective one of the plurality of radial layers, and the density of the completed bale.

2. The round baler system set forth in claim 1, further comprising a moisture sensor operable to detect data related to a moisture content of the crop material for each respective one of the plurality of radial layers.

3. The round baler system set forth in claim 2, wherein the processor is operable to execute the yield mapping algorithm to determine a moisture content of the crop material of the respective one of the plurality of radial layers during formation of the current bale with data received from the moisture sensor.

4. The round baler system set forth in claim 3, wherein the processor is operable to execute the yield mapping algorithm to estimate the density of the respective one of the plurality of radial layers during formation of the current bale based on the moisture content of the respective one of the plurality of radial layers.

5. The round baler system set forth in claim 1, wherein the processor is operable to execute the yield mapping algorithm to determine a field origin location of the respective one of the plurality of radial layers during formation of the current bale.

6. The round baler system set forth in claim 5, wherein the processor is operable to execute the yield mapping algorithm to generate a yield map of the field based on the estimated density and the field origin location of the respective one of the plurality of radial layers during formation of the current bale.

7. The round baler system set forth in claim 6, wherein the processor is operable to execute the yield mapping algorithm to control a function of the baler system based on the yield map of the field.

8. The round baler system set forth in claim 1, wherein the processor is operable to execute the yield mapping algorithm to estimate the density of the respective one of the plurality of radial layers during formation of the current bale based on the density of at least two previously completed bales.

9. The round baler system set forth in claim 1, wherein the processor is operable to execute the yield mapping algorithm to estimate a density of each of the plurality of radial layers of the current bale during formation of the current bale based on the respective volume of each of the plurality of radial layers of the current bale and the density of the completed bale.

10. The round baler system set forth in claim 9, wherein the processor is operable to execute the yield mapping algorithm to estimate the density of each of the plurality of radial layers of the current bale during formation of the current bale based on a respective diametric size of each of the plurality of radial layers of the current bale.

11. The round baler system set forth in claim 10, wherein the processor is operable to execute the yield mapping algorithm to estimate the density of each of the plurality of radial layers of the current bale during formation of the current bale by multiplying the estimated density of each respective one of the plurality of radial layers by a density factor based on the diametric size of that respective radial layer, wherein the density factor includes a number equal to or less than one.

12. A round baler system comprising:
a pick-up operable to gather and move crop material while traversing a field;
a baler system having a baling chamber configured to receive a flow of material from the pick-up and roll the incoming flow of crop material in a spiral fashion into a bale having a cylindrical shape, wherein the bale includes a plurality of radial layers;
a bale size sensor operable to detect data related to a radial size of the bale during formation thereof;
a moisture sensor operable to detect data related to a moisture content of the crop material for each respective one of the plurality of radial layers;
a bale weight sensor operable to detect data related to a weight of a completed bale;
a location sensor operable to determine a respective field origin location of the crop material gathered by the pick-up for each respective one of the plurality of radial layers;
a controller including a processor and a memory having a yield mapping algorithm stored thereon, wherein the processor is operable to execute the yield mapping algorithm to:
calculate a density of a completed bale with data received from the bale weight sensor and the bale size sensor;
determine a volume of a respective one of the plurality of radial layers during formation of a current bale subsequent to the completed bale with data received from the bale size sensor;
determine a moisture content of the crop material of the respective one of the plurality of radial layers during formation of the current bale with data received from the moisture sensor;
estimate a density of the respective one of the plurality of radial layers during formation of the current bale based on the volume and the moisture content of the respective one of the plurality of radial layers, and the density of the completed bale;
determine a field origin location of the respective one of the plurality of radial layers during formation of the current bale; and
generate a yield map of the field based on the estimated density and the field origin location of the respective one of the plurality of radial layers during formation of the current bale.

13. The round baler system set forth in claim 12, wherein the processor is operable to execute the yield mapping algorithm to control a function of the baler system based on the yield map of the field.

14. The round baler system set forth in claim 12, wherein the processor is operable to execute the yield mapping algorithm to estimate the density of the respective one of the plurality of radial layers during formation of the current bale based on the density of at least two previously completed bales.

15. The round baler system set forth in claim 12, wherein the processor is operable to execute the yield mapping algorithm to estimate a density of each of the plurality of radial layers of the current bale during formation of the current bale based on the respective volume of each of the plurality of radial layers of the current bale, the respective moisture content of each of the plurality of radial layers of the current bale, and the density of the completed bale.

16. The round baler system set forth in claim 15, wherein the processor is operable to execute the yield mapping algorithm to estimate the density of each of the plurality of radial layers of the current bale during formation of the current bale by multiplying the estimated density of each respective one of the plurality of radial layers by a density factor based on the diametric size of that respective radial layer, wherein the density factor includes a number equal to or less than one.

17. A method of generating a yield map of crop material formed into a round bale, the method comprising:
completely forming a first bale in a baling chamber of a baler system;
calculating a density of the first bale;

forming a second bale in the baling chamber of the baler system, wherein the second bale includes a plurality of radial layers;

determining a volume of a respective one of the plurality of radial layers of the second bale during formation of the second bale subsequent to the completed first bale with data received from a bale size sensor;

determining a moisture content of the crop material of the respective one of the plurality of radial layers of the second bale during formation of the second bale with data received from a moisture sensor;

estimating a density of the respective one of the plurality of radial layers of the second bale during formation of the second bale based on the volume and the moisture content of the respective one of the plurality of radial layers of the second bale, and the density of the completed first bale;

determining a field origin location of the respective one of the plurality of radial layers of the second bale during formation of the second bale; and generating the yield map of the field based on the estimated density and the field origin location of the respective one of the plurality of radial layers of the second bale during formation of the second bale.

18. The method set forth in claim 17, further comprising controlling a function of the baler system based on the yield map of the field.

19. The method set forth in claim 17, further comprising multiplying the estimated density of each respective one of the plurality of radial layers by a density factor based on the diametric size of that respective radial layer, wherein the density factor includes a number equal to or less than one.

* * * * *